(12) United States Patent
Bastia

(10) Patent No.: US 11,170,893 B2
(45) Date of Patent: Nov. 9, 2021

(54) SYSTEM FOR MANAGING USE OF MEDICAL DEVICES

(71) Applicant: THD S.P.A., Correggio (IT)

(72) Inventor: Filippo Bastia, Soliera (IT)

(73) Assignee: THD S.P.A., Correggio (IT)

( * ) Notice: Subject to any disclaimer, the term of this patent is extended or adjusted under 35 U.S.C. 154(b) by 931 days.

(21) Appl. No.: 15/151,961

(22) Filed: May 11, 2016

(65) Prior Publication Data
US 2016/0338794 A1      Nov. 24, 2016

(30) Foreign Application Priority Data

May 20, 2015    (IT) .................. 102015000016084

(51) Int. Cl.
*G16H 40/63*     (2018.01)
*G16H 40/40*     (2018.01)
(Continued)

(52) U.S. Cl.
CPC ............. *G16H 40/63* (2018.01); *A61B 5/036* (2013.01); *A61B 5/1107* (2013.01); *A61B 5/4255* (2013.01); *A61B 90/08* (2016.02); *A61B 90/98* (2016.02); *G16H 40/20* (2018.01); *G16H 40/40* (2018.01); *A61B 2017/0023* (2013.01); *A61B 2017/00132* (2013.01);
(Continued)

(58) Field of Classification Search
CPC combination set(s) only.
See application file for complete search history.

(56) References Cited

U.S. PATENT DOCUMENTS 6,308,089 B1 * 10/2001 von der Ruhr et al.
7,568,619 B2     8/2009 Todd et al.
(Continued)

FOREIGN PATENT DOCUMENTS

CN     1356783 A     7/2002
CN     1733339 A     2/2006
(Continued)

OTHER PUBLICATIONS

Anonymous; "Esophogeal/Rectal Temperature Probe Disposable, 9 FR, Sterilized, Continuous Monitoring"; Philips; XP002753084; Jan. 1, 2014; http:www8.healthcare.philips.com/MySupplies/Products/Details.aspx?id=M1837A—Retrieved from Internet on Jan. 18, 2016, pp. 1-3.

*Primary Examiner* — Michael Tomaszewski
*Assistant Examiner* — William T. Monticello
(74) *Attorney, Agent, or Firm* — Pearne & Gordon LLP

(57) ABSTRACT

A system and method for managing use of medical devices. The system includes: an apparatus intended to be used in combination with one or more medical devices; one or more processing units; authorizing means, which may be associated to a medical device and including one identifier parameter able to uniquely identify said device. The processing unit includes: one reader module configured for acquiring the identifier parameter from the authorizing means; one enabling module configured to allow or inhibit use of the device with the apparatus on the basis of control parameters; and at least one calculation module configured for setting the number of uses of the device. The control parameters include the identifier parameter acquired and the number of uses calculated.

9 Claims, 3 Drawing Sheets

(51) Int. Cl.

| | |
|---|---|
| *G16H 40/20* | (2018.01) |
| *A61B 90/00* | (2016.01) |
| *A61B 90/98* | (2016.01) |
| *A61B 5/03* | (2006.01) |
| *A61B 5/11* | (2006.01) |
| *A61B 5/00* | (2006.01) |
| *A61B 17/00* | (2006.01) |

(52) U.S. Cl.
CPC ........... *A61B 2090/0803* (2016.02); *A61B 2090/0814* (2016.02); *A61B 2560/0475* (2013.01); *G06Q 2220/00* (2013.01)

(56) References Cited

U.S. PATENT DOCUMENTS

| | | | |
|---|---|---|---|
| 7,752,058 | B2 | 7/2010 | Sasaki et al. |
| 7,835,927 | B2 | 11/2010 | Schlotterbeck et al. |
| 7,934,648 | B2 | 5/2011 | Charles et al. |
| 8,069,735 | B1 * | 12/2011 | Egorov |
| 9,649,014 | B2 * | 5/2017 | Ouyang et al. |
| 2002/0065685 | A1 | 5/2002 | Sasaki et al. |
| 2002/0096180 | A1 * | 7/2002 | Teller |
| 2003/0023460 | A1 | 1/2003 | Ackermann et al. |
| 2004/0122419 | A1 | 6/2004 | Neuberger |
| 2004/0128162 | A1 | 7/2004 | Schlotterbeck et al. |
| 2006/0111699 | A1 | 3/2006 | Neuberger |
| 2006/0129140 | A1 | 6/2006 | Todd et al. |
| 2007/0260489 | A1 | 11/2007 | Sasaki et al. |
| 2007/0260490 | A1 | 11/2007 | Sasaki et al. |
| 2008/0054073 | A1 | 3/2008 | Charles et al. |
| 2011/0060758 | A1 | 3/2011 | Schlotterbeck et al. |
| 2015/0199487 | A1 * | 1/2015 | Grauds et al. |
| 2015/0242581 | A1 * | 3/2015 | Talbert et al. |
| 2015/0112231 | A1 * | 4/2015 | Iglesias |
| 2016/0267295 | A1 * | 9/2016 | Gervais et al. |
| 2018/0353073 | A1 * | 12/2018 | Boucher et al. |

FOREIGN PATENT DOCUMENTS

| | | |
|---|---|---|
| CN | 1759398 A | 4/2006 |
| CN | 101252890 A | 8/2008 |
| WO | 2004060140 A2 | 7/2004 |
| WO | 2006066035 A2 | 6/2006 |

\* cited by examiner

SYSTEM FOR MANAGING USE OF MEDICAL DEVICES

FIELD OF THE INVENTION

The invention has for object a system and a method for managing use of medical devices.

In particular, the invention relates to a system and a method for preventing unauthorized reuse of medical devices.

The invention is devised to be particularly, but not exclusively, employed in clinical anorectal examinations, with particular reference to anorectal manometry.

DESCRIPTION OF RELATED ART

For clinical assessment of the state of health of the anal sphincter, several tests are currently effected, which include the manometric measurement, in order to assess ability of the sphincter muscles to exert sufficient closing pressure for retaining solids, liquids and gases.

The manometric measurement is carried out by using medical devices, such as probes or catheters to be introduced into the anal canal.

In the application field of the invention, for reasons of hygiene and convenience of use, it has long felt the need to have available disposable medical devices, of which one may prevent unauthorized re-use.

This need still remains unsatisfied, since any reliable system to prevent unauthorized reuse of these devices is available on the market.

SUMMARY OF THE INVENTION

In this context, the technical task underlying the present invention is to propose a system and a method for managing use of medical devices which are able to fulfill the need referred to above.

The technical task mentioned is achieved by the system and method for managing use of medical devices implemented in accordance with claim 1 and claim 14 respectively.

BRIEF DESCRIPTION OF THE DRAWINGS

Further characteristics and advantages of the present invention will become more apparent from the indicative, and therefore non-limiting description of a preferred but non-exclusive embodiment of the system of the invention, illustrated in the accompanying drawings wherein.

DETAILED DESCRIPTION OF PREFERRED EMBODIMENTS OF THE INVENTION

Figure 1:
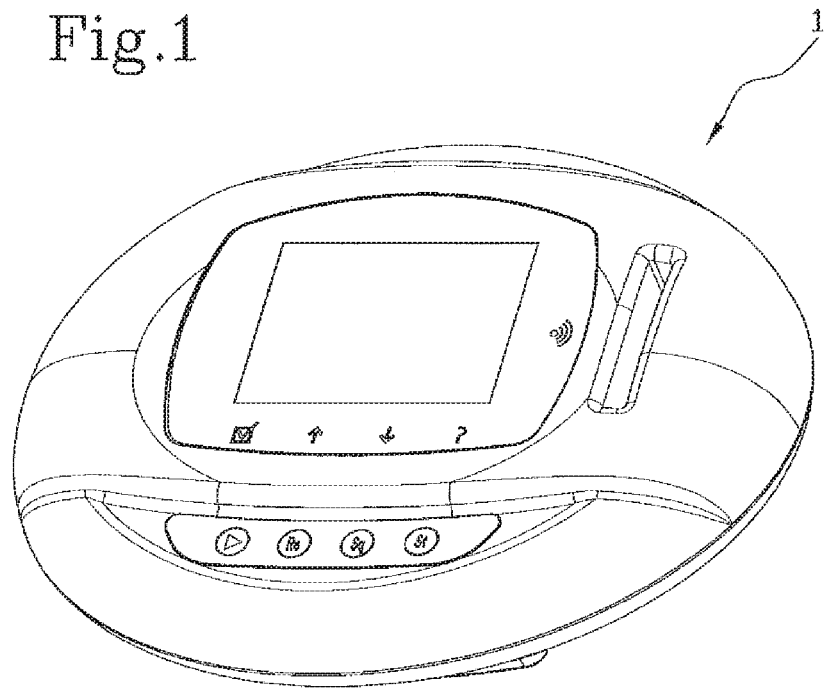
FIG. 1 is an axonometric view of an apparatus comprised in the system of the invention in an operative rest configuration thereof.
Figure 2:
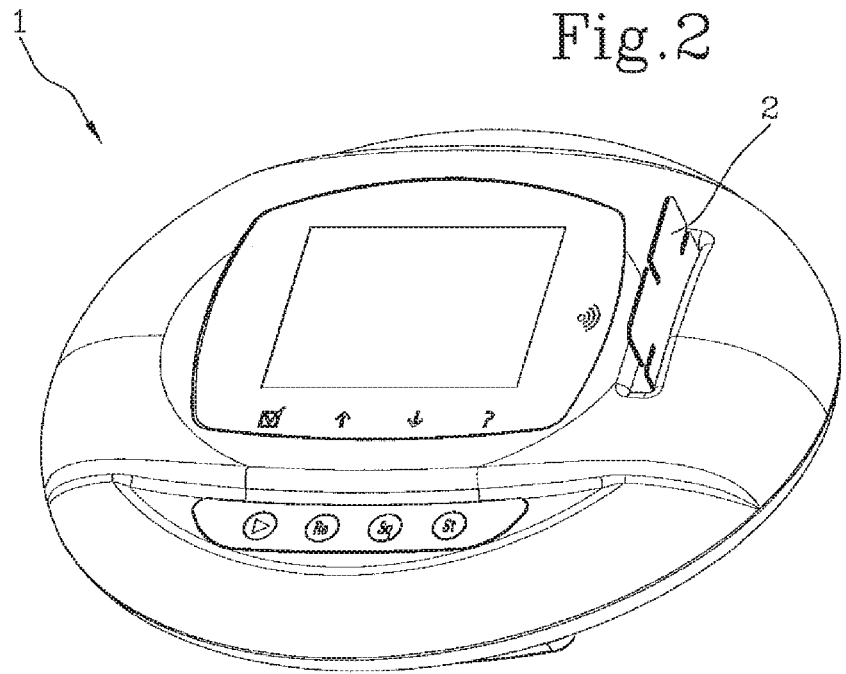
FIG. 2 is the view of FIG. 1, wherein the apparatus is associated with authorizing means in an operative working configuration thereof.

With reference to the attached figures, by 1 it is indicated an apparatus designed for use in the biomedical field comprised within the management system of the invention.

The system 1, 2 proposed is designed to manage use of medical devices 3 and in particular to prevent unauthorized re-use of such devices. In detail, the invention is especially intended to ensure that all and any disposable medical devices 3 are used only once.

The above apparatus 1 is devised for co-operating functionally with the medical device 3, for example to allow use thereof in diagnostic examinations.

The invention comprises one or more processing units 10.

In general, it should be noted that in the present description the processing unit is disclosed as divided into distinct functional modules for the purposes of describing features thereof in a clear and complete manner.

In practice, such a processing unit may be constituted by a single device or apparatus, or a suitably programmed electronic system to perform the described functions.

The various modules may correspond to hardware entity and/or software routines.

Alternatively or in addition, such functions may be performed by a plurality of electronic devices, whereon for example, aforesaid functional modules can be distributed.

In general, the processing unit may use one or more micro-processors or micro-controllers or the like for the execution of instructions contained, for example, in the memory modules.

In a particular embodiment of the invention shown in the figures, the medical device 3 is an anorectal probe.

In this case, the apparatus 1 is of the type suitable to allow operation of the probe 3 and to acquire detections thereof.

Preferably, as mentioned above, the probes 3 are disposable and the invention is designed to prevent re-use of a probe 3 on the same patient or even on other patients, which was already employed for effecting an examination on a patient, for example, an anorectal manometry.

In practice, in the embodiment shown in the enclosed drawings, the apparatus 1 is a tester which includes, in addition to its own processing unit 10, the means necessary to the operation of the probe, the measuring means for acquiring the diagnostic data, a protective casing, any feeding means, user interface means, etc.

According to an important aspect of the invention, the system 1, 2 comprises authorizing means 2, associable to respective medical devices 3 and comprising at least one identifier parameter able to uniquely identify the relative device 3.

In practice, this identifier parameter may contain a serial number or at least a code based on which identity of a specific device 3 can be detected in a certain and unambiguous manner.

In the example illustrated in the figures, the authorizing means comprises a card 2 including by way of example a RFID transponder, wherein the identifier parameter is stored.

In this case, a card 2 can be made available coupled to the respective medical device 3 (such as an anorectal probe) for example included in the same package.

Preferably, the authorizing means 2 comprises its own memory unit that includes at least the pre-recorded identifier parameter; according to an optional embodiment, the authorizing means 2 could include a processing unit thereto related provided with one or more operating and/or memory modules.

Where RFID technology is used, the above-mentioned memory unit is that comprised within said transponder.

The processing unit 10 of the apparatus 1 comprises first of all a reader module 11 configured for acquiring the identifier parameter by the authorizing means 2.

In the case in which the authorizing means 2 includes the RFID transponder, the reader module 11 is of the type suitable for a contactless reading to radio frequency.

The invention further provides a calculation module 21 configured to determine the number of times that the device 3 has been used with the apparatus 1.

Although such calculation module 21 is preferably comprised in the memory unit of the authorizing means 2, it is not excluded that the calculation module 21 may reside in the processing unit 10 of the apparatus 1.

The invention advantageously provides one enabling module 13, configured for allowing or inhibiting use of the device 3 with the apparatus 1 based on the control parameters.

Among the control parameters verified by the enabling module 13, there are at least the identifier parameters acquired by the reader module 11 and the number of uses of a given device 3 calculated by the calculation module 21.

In practice, the enabling module 13 allows use of the device 3, for example within a diagnostic test, only if pre-programmed conditions are observed.

In detail, the enabling module 13 first checks whether the identifier parameter is acceptable (which aspect shall be detailed later).

Where the device 3 associated to the identifier, classified as acceptable, was already used for the maximum number of times permitted, then the enabling module 13 inhibits use of the device 3.

The maximum number of times that a given device 3 can be used is pre-set and, in the case of disposable devices, this number is equal to one; However, more generally, the maximum number of uses allowed can also be greater than one.

In the preferred embodiment of the invention, the enabling module 13 comprises a comparison module 131 configured to check whether an acquired identifier parameter falls within a set of acceptable parameters and if the number of uses calculated exceeds the maximum number of uses permitted.

The acceptable parameters and the maximum number of uses are recorded, i.e. pre-programmed or pre-defined, on one or more memory modules.

Preferably, the processing unit 10 of the apparatus 1 includes at least one memory module 14, whereon the set of acceptable parameters is stored. In practice, the processing unit 10 "knows" the identifier parameters of the devices that can be used.

In addition, aforesaid calculation module 21 preferably comprises a counter module 211 configured to count the number of times that a specific identifier parameter was acquired and recognized as acceptable by said comparison module 131.

In a preferential embodiment, this calculation module 21 is comprised within said memory unit of the authorizing means 2.

In detail, the memory unit of the authorizing means 2 is configured to record the number of uses of a given device 3 and includes, pre-recorded, the value of the maximum number of uses permitted.

When an identifier parameter is acquired by the reader module 11, the identifier parameter is compared with those acceptable.

If that specific identifier parameter is "recognized" as valid, the invention verifies the number of times that the respective device 3 was employed.

In the case where the specified device 3 was already used for the maximum number of uses allowed, the enabling module 13 does not enable use of the apparatus 1 and thus it does not allow use of the medical device 3, in particular for the purposes of effecting a diagnostic examination.

Otherwise, the counter module 211 provides to record another authorized use of the device 3 concerned.

Additionally, the calculation module 21 preferably comprises a timer module 212 configured to establish usage duration of a device 3.

This measure may prevent the user, generally a physician, from using the device 3 for effecting several examinations consecutively without the apparatus 1 having been switched off.

In order to prevent violation of the system 1, 2, it is provided that the information contained on the authorizing means 2 are encrypted.

In other words, cryptographic systems may be employed for encoding the various information and parameters included in the memory unit of the authorizing means 2.

In this case, the processing unit 10 may comprise a decryption module 111 that may in turn be embedded within the reader module 11 or co-operate with the latter and that is configured for decoding encrypted information and parameters.

Here below operation of the invention is disclosed based on the case of example wherein the system 1, 2 is predisposed for use of anorectal disposable probes 3 and wherein, therefore, the enabling module 13 of the processing unit 10 is configured for inhibiting use of the apparatus 1, thereby preventing the diagnostic execution of the examination once the calculation module 21 has calculated that the probe 3 intended to be used has already been employed once.

Figure 3:
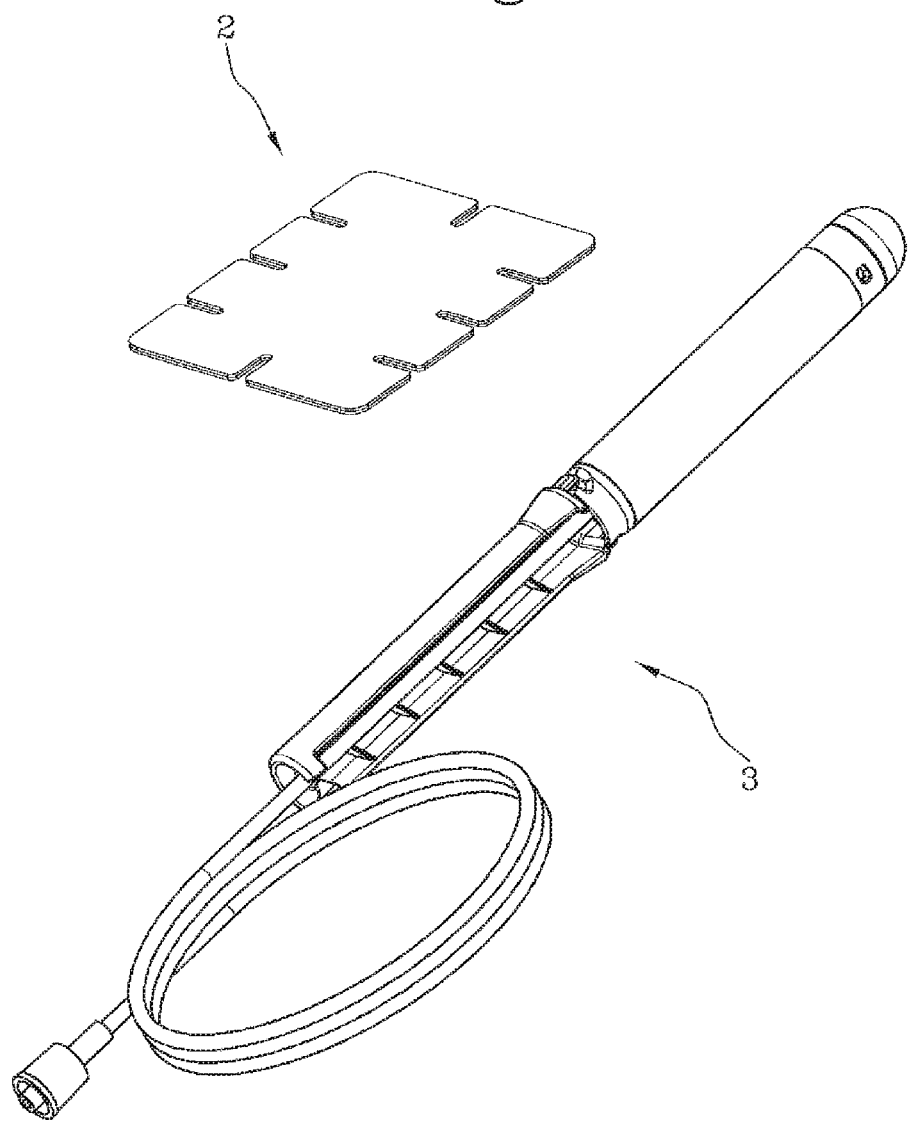
FIG. 3 is an isometric view of a medical device and authorizing means associated therewith.
Figure 4:
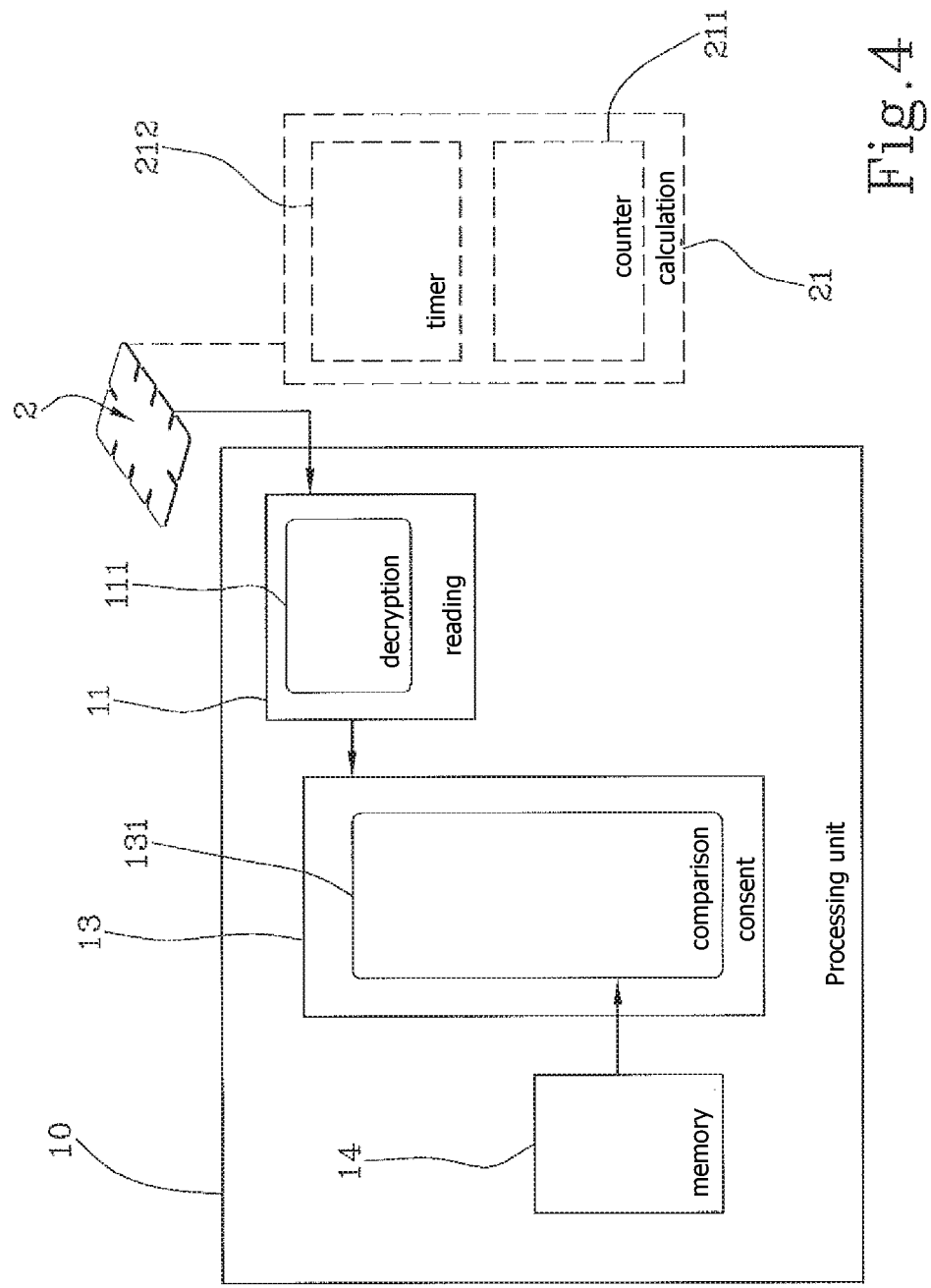
FIG. 4 is a schematic representation of the operating modules and memory modules employed in the invention.

The physician opens a package containing a probe 3 and the card 2 uniquely associated therewith (shown by way of example in FIG. 3).

After that, the probe 3 is connected by the physician to the apparatus 1 or tester (for example via a Luer-lock connector) and the card 2 is placed at a zone of the tester 1 wherein the processing unit 10 can read the serial number (or other identifier parameter) recorded in the card 2.

In the case depicted in FIG. 3, such a zone is defined within an insertion slot of the card 2 which is afforded on the casing of the tester 1; however; this is not a binding configuration.

The processing unit 10 reads the card 2 and makes use of the probe 3 available, provided that a serial number is detected as acceptable by the processing unit 10 and the related probe 3 was not already previously used.

The examination effected by the physician then has a maximum pre-fixed duration.

Once said examination is over, and in any case on expiry of that period of maximum duration, the processing unit 10 of the tester 1 no longer allows use of the card 2.

Hence, in order that a new examination is performed, the physician will have to open a new package containing a fresh card 2 with RFID (or other authorizing means) and a fresh probe 3, i.e. never used before.

The invention is further configured as a method for managing use of medical devices 3, implementable via the system 1, 2 disclosed above. The proposed method, which is especially provided to prevent unauthorized re-use of medical devices 3, comprises the following steps: making available authorizing means 2 associated to a medical device 3 and comprising at least one identifier parameter which is able to uniquely identify the device 3;

acquiring an identifier parameter by said authorizing means 2; establishing the number of uses of the device 3;

allowing or inhibiting use of the device 3 on the basis of control parameters comprising the identifier parameter acquired and the number of uses calculated.

It should be appreciated that the functions of the processing unit 10 and the authorizing means 2 described above, in particular as defined by the operating and memory modules previously mentioned, may define corresponding actions that represent optional steps of the method of the invention.

The proposed method can be implemented by means of a computer program executed on a processing system, which program can be made available on a medium readable by a computer.

The invention claimed is:

1. A system for managing use of disposable anorectal probes, comprising:
   an apparatus;
   one or more processing units; and
   a kit comprising (i) a disposable anorectal probe and (ii) authorizing means comprising a card with a respective memory unit, wherein the card is associated to the disposable anorectal probe and configured to prevent use of the probe if the probe was used in a previous diagnostic examination, the authorizing means comprising at least one identifier parameter able to univocally identify said probe, wherein said memory unit stores a pre-recorded value of a maximum number of uses of the probe allowed and is configured for recording a number of uses of the probe, and wherein said memory unit comprises at least one calculation module that is configured for setting the number of uses of the probe;
   wherein the one or more processing units of the system are configured for inhibiting use of the apparatus based on control parameters comprising the identifier parameter acquired and the number of uses of the disposable anorectal probe calculated,
   wherein said one or more processing units comprise:
   at least one reader module configured for acquiring said identifier parameter from said authorizing means; and
   at least one enabling module comprising a comparison module configured for checking whether an identifier parameter acquired is comprised within a set of acceptable parameters and whether the number of uses calculated exceeds the maximum number of uses of the probe allowed, said set of acceptable parameters and said maximum number of uses of the probe allowed being recorded on one or more memory modules, wherein the enabling module is configured for enabling or preventing use of the probe in combination with said apparatus on the basis of said control parameters, and further configured for preventing use of the apparatus in combination with the probe if the calculation module has determined that the probe was already used once.

2. The system according to claim 1, wherein said calculation module comprises a counter module configured for determining how many times a specific identifier parameter has been acquired and recognized as acceptable by said comparison module.

3. The system according to claim 1, wherein said calculation module comprises a timer module configured for determining usage duration of the probe.

4. The system according to claim 3, wherein the control parameters include usage duration calculated by the timer module.

5. The system according to claim 1, wherein at least a processing unit comprises a decryption module.

6. The system according to claim 1, wherein said authorizing means further comprises a RFID transponder, said reader module including means for reading RFID transponders.

7. The system according to claim 1, wherein the apparatus is of the type suitable for enabling operation and acquiring detections of said probe.

8. A method for managing use of disposable anorectal probes, comprising use of the system of claim 1 and the following steps:
   acquiring the identifier parameter from said authorizing means;
   setting the maximum number of uses of the probe;
   enabling or preventing use of the probe on the basis of control parameters comprising the identifier parameter acquired and the number of uses of the probe calculated.

9. A computer program providing the steps of the method according to claim 8.

* * * * *